United States Patent [19]
Kobatake et al.

[11] Patent Number: 5,720,276
[45] Date of Patent: Feb. 24, 1998

[54] APPARATUS FOR SUPPLYING A RESPIRATORY GAS TO A PATIENT

[75] Inventors: Daisuke Kobatake; Kenji Takemasa, both of Yamaguchi, Japan

[73] Assignee: Teijin Limited, Osaka, Japan

[21] Appl. No.: 547,782

[22] Filed: Oct. 25, 1995

[30] Foreign Application Priority Data

Oct. 25, 1994 [JP] Japan .................. 6-260123
Jan. 11, 1995 [JP] Japan .................. 7-002598

[51] Int. Cl.⁶ .................................. A61M 16/00
[52] U.S. Cl. .................. 128/204.18; 128/204.21; 128/204.26
[58] Field of Search .............. 128/204.18, 204.21, 128/204.23

[56] References Cited

U.S. PATENT DOCUMENTS

| | | | |
|---|---|---|---|
| 3,493,703 | 2/1970 | Finan | 128/204.26 |
| 4,461,293 | 7/1984 | Chen | 128/204.23 |
| 4,570,631 | 2/1986 | Durkan | 128/204.23 |
| 4,681,099 | 7/1987 | Sato et al. | 128/204.23 |
| 4,686,974 | 8/1987 | Sato et al. | |
| 4,838,261 | 6/1989 | von den Hagen | 128/204.18 |
| 4,932,402 | 6/1990 | Snook et al. | 128/204.23 |
| 5,005,570 | 4/1991 | Perkins | 128/204.23 |
| 5,038,770 | 8/1991 | Perkins | 128/204.18 |
| 5,038,771 | 8/1991 | Dietz | 128/204.21 |
| 5,048,515 | 9/1991 | Sanso | 128/204.26 |
| 5,099,837 | 3/1992 | Russel, Sr. et al. | 128/204.18 |
| 5,211,170 | 5/1993 | Press | 128/204.23 |
| 5,303,699 | 4/1994 | Bonassa et al. | 128/204.21 |

FOREIGN PATENT DOCUMENTS

| | | |
|---|---|---|
| 0099283 | 1/1984 | European Pat. Off. . |
| 0285470 | 10/1988 | European Pat. Off. . |
| 4309923 | 9/1994 | Germany . |
| 5156 | 1/1993 | Japan . |
| 8706142 | 10/1987 | WIPO . |

*Primary Examiner*—Aaron J. Lewis
*Attorney, Agent, or Firm*—Sughrue, Mion, Zinn, Macpeak & Seas, PLLC

[57] ABSTRACT

An apparatus for supplying a respiratory gas to a patient includes a respiratory gas generating device, a device for introducing the respiratory gas into the cavitas nasi of the patient, a conduit fluidly connected to the respiratory gas generating device and the introducing device; a valve, provided in the conduit, for separating and connecting the introducing device from and to the respiratory gas generating device and an orifice provided in the conduit upstream of the valve means. The apparatus for supplying the respiratory further includes a controller for operating the valve between intermittent and continuous mode. In the intermittent mode, the valve connects the introducing device to the respiratory gas generating device at a predetermined interval to provide the respiratory gas in the form of a pulse, and in the continuous mode, the valve continuously connects the introducing device to the respiratory gas generating device. The valve is provided in the conduit adjacent to the introducing device to allow the pressure pulse of the respiratory gas to reach the introducing device a delay no greater than 20 msec.

19 Claims, 10 Drawing Sheets

1

APPARATUS FOR SUPPLYING A RESPIRATORY GAS TO A PATIENT

BACKGROUND OF THE INVENTION

(1) Field of the Invention

The invention relates to an apparatus for supplying a respiratory gas to a patient.

(2) Description of the Related Art

An apparatus is known for supplying a respiratory gas, in particular an oxygen-enriched gas, to a patient, which, typically, comprises an oxygen gas source such as an oxygen gas bottle or an apparatus for producing an oxygen-enriched gas by removing nitrogen from the air, a nasal cannula, which is adapted to be inserted into the cavitas nasi of the patient, for introducing the oxygen gas, a conduit or a tube connected to the discharge port of the oxygen bottle and the nasal cannula, and a control valve, provided in the conduit or the tube, for fluidly separating and connecting between the oxygen bottle and the nasal cannula.

The control valve opens when an inspiration phase starts, and then closes after a predetermined time has passed before the sequential expiration phase. Thus, the control valve opens during the predetermined time to save the gas consumption, pressurized oxygen gas or oxygen-enriched gas is supplied to the patient since the supplied gas at the last stage of the inspiration phase is exhausted by the expiration gas from the lungs of the patient before it reaches the lungs. In general, the control valve is mounted to a carrier cart or a housing of the oxygen-enriched gas generator. Japanese Unexamined Patent Publication (Kokai) No. 1-221170 discloses an example of such an apparatus, in which the control valve is controlled by detecting the respiration phase and, in particular, by detecting the moment of the start of inspiration.

A long tube is often used to extend the action range of the patient. In this case, the distance between the discharge port of the control valve and the discharge end of the nasal cannula becomes long compared with the usual application. This deteriorates the sensitivity of the detection. Further, the appropriate pulse of the pressurized oxygen-enriched gas cannot be obtained due to a delay before the pressurized gas reaches the discharge ends of the nasal cannula from the discharge port of the control valve.

SUMMARY OF THE INVENTION

The invention is directed to solve the above problem in the prior art.

The invention provides an apparatus for supplying a respiratory gas to a patient. The apparatus comprises means for generating a respiratory gas; means for introducing the respiratory gas into the cavitas nasi of the patient; and a conduit fluidly connected to the respiratory gas generating means and the introducing means. The introducing means includes an output port which is adapted to be inserted into the cavitas nasi of the patient. The apparatus further comprises a valve means, which is provided in the conduit, for separating and connecting the introducing means from and to the respiratory gas generating means; an orifice provided in the conduit upstream of the valve means; and means for controlling the operation of the valve means between intermittent and continuous mode. In the intermittent mode, the valve means connects the introducing means to the respiratory gas generating means at a predetermined interval to provide the respiratory gas in the form of a pulse, and in the continuous mode, the valve means continuously connects the introducing means to the respiratory gas generating means.

The valve means can be preferably provided in the conduit adjacent to the introducing means to allow the pressure pulse of the respiratory gas to reach the output port of the introducing means without a delay grater than 40 msec. Further, the valve means may be provided in the conduit within 2 m from the end of the discharge port. The valve means can be formed by any type of device which can fluidly separate and connect the introducing means from and to the respiratory gas generating means.

In another feature of the invention, the valve means connects the introducing means to the respiratory gas generating means during a predetermined time, preferably, at most one third of the interval of the respiration phase, after the inspiration phase is detected.

In another feature of the invention, the apparatus further comprises an orifice provided in the conduit upstream of the valve means. Preferably, an accumulator means is provided in the conduit between the orifice and the valve means.

In another feature of the invention, the apparatus further comprises a first and second branches which are divided from the conduit, first and second flow reducers which are provided in the first and second branch conduits respectively; and a directional valve means for selecting one of the first and second branch conduits through which the respiration gas flows to the patient. Means for determining whether the continuous mode or intermittent mode is selected, and the directional valve means allows the respiratory gas to flow through the first branch conduit during the continuous mode, and to flow through the second branch conduit during the intermittent mode. The first flow reducer advantageously reduces the flow rate of the respiratory gas more than the second flow reducer.

In another feature of the invention, the apparatus further comprises a manual control unit which is adapted to be put adjacent to or on the patient. The manual control unit comprises a housing in which the shut-off valve is provided; an inlet connector to which the conduit is connected; an outlet connector to which the introducing means is connected; a selector switch for manually selecting the operational mode between the intermittent and continuous modes; and an interval input device for selecting the interval during which the shut-off valve connects the introducing means to the respiratory gas generating means.

BRIEF DESCRIPTION OF THE DRAWINGS

These and other objects and advantages and further description will now be discussed in connection with the drawings in which.

DESCRIPTION OF THE PREFERRED EMBODIMENTS

Figure 1:
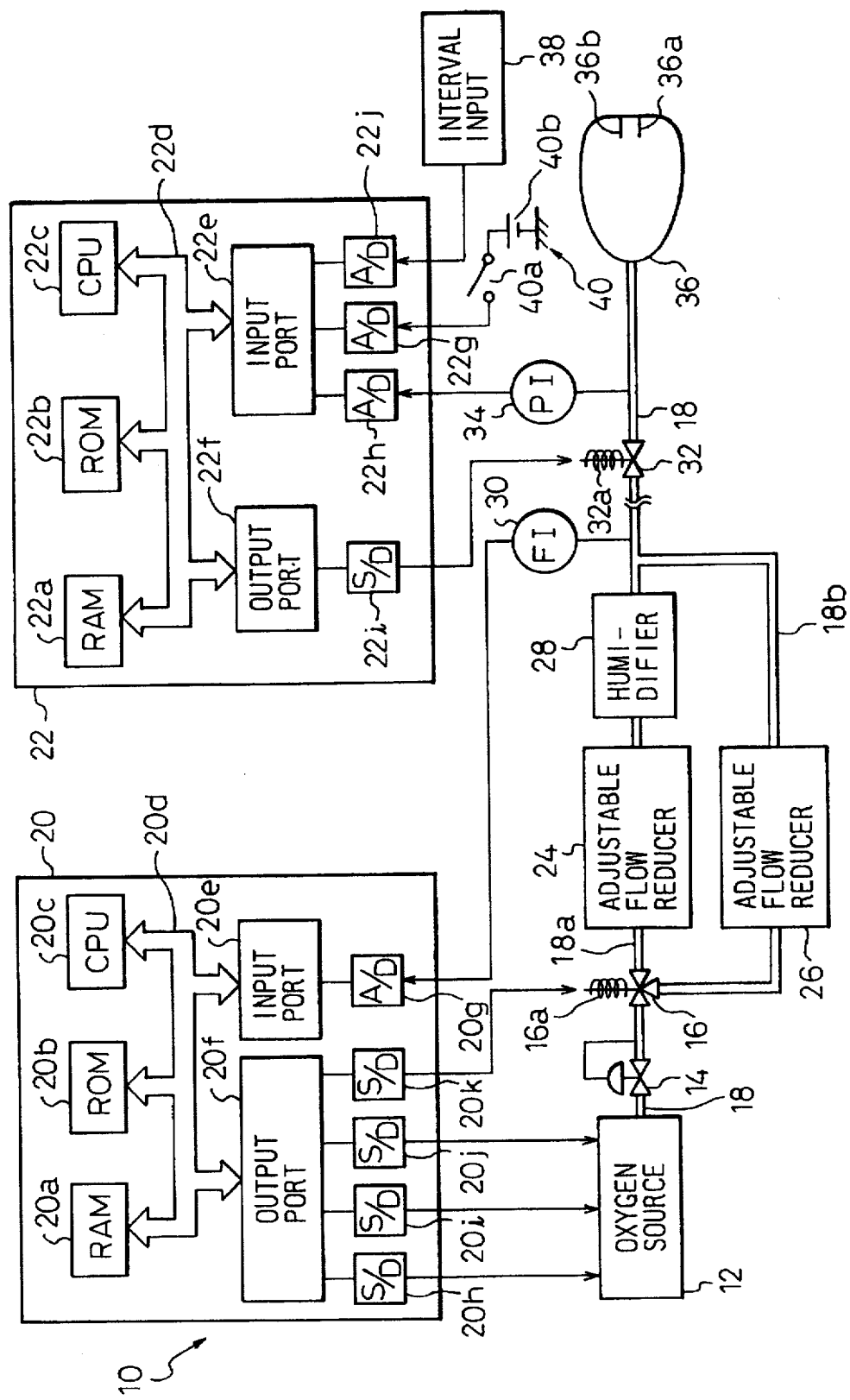
FIG. 1 is schematic diagram of an apparatus according to the first embodiment of the invention.

In FIG. 1, an apparatus 10, according to the first embodiment of the invention, for supplying a respiration gas to a patient, will be described. The apparatus 10 comprises an oxygen gas source 12 which generates an oxygen-enriched gas as a respiration gas. The oxygen gas source 12 can be of any type, such as an oxygen bottle, which generates a gas suitable for respiration. However, in this embodiment, the oxygen gas source 12 generates an oxygen-enriched gas by absorbing a portion of nitrogen in the air. The detailed constitution of the oxygen gas source 12 will be described herein after.

The oxygen gas source 12 is controlled by a first controller 20. The first controller comprises a random access memory (RAM) 20a, a read-only memory (ROM) 20b, central processing unit (CPU) 20c, an output port 20f and an input port 20e which are connected to each other by a bidirectional bus 20d. The oxygen gas source 12 is connected to the output port 20f through solenoid drivers 20h, 20i and 20j. The oxygen gas source 12 may be controlled by another type of controller.

Figure 2:
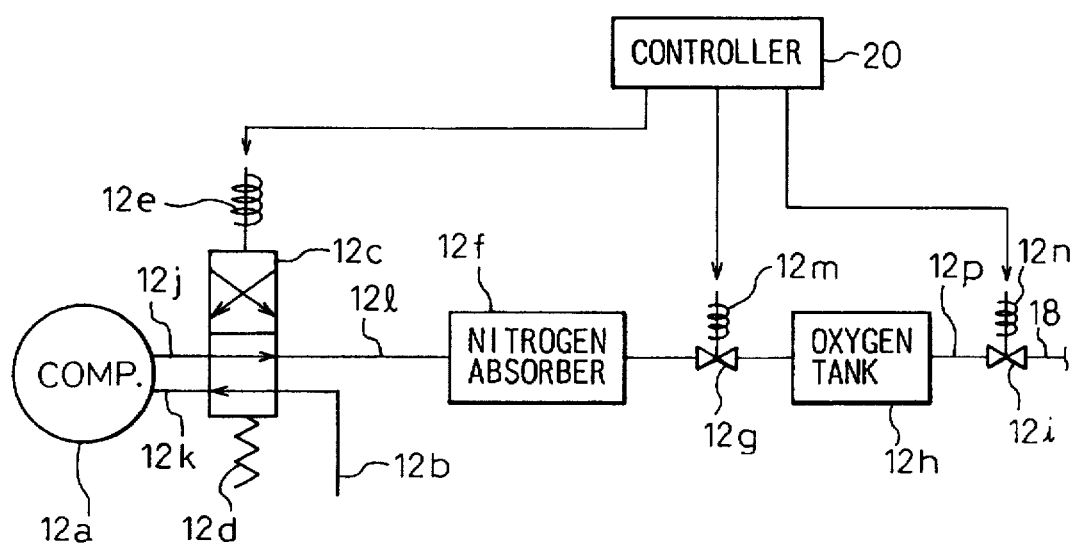
FIG. 2 is schematic diagram of an oxygen-enriched gas generating system which is used for the invention.

In FIG. 2, an example for the oxygen source 12 is illustrated. The oxygen source 12 is controlled by the first controller 20 and comprises a compressor 12a of a conventional type, nitrogen absorber 12f, and an oxygen tank 12h which are connected to each other by a conduit 12l. The compressor 12a includes discharge and suction ports 12j and 12k which are connected to a solenoid operated directional control valve 12c.

The directional control valve 12c has first and second positions. At the first position, the discharge port 12j of the compressor 12a is connected to the nitrogen absorber 12f, and the suction port 12k communicates with ambient through the directional control valve 12c and an additional conduit 12b as shown in FIG. 2. At the second position, the discharge port 12j communicates with the ambient, and the suction port 12k is connected to the nitrogen absorber 12f. The solenoid operated directional control valve 12c includes a spring 12d for biasing a valve element (not shown) to the first position, and a first solenoid 12e which is connected to the output port 20f of the first controller 20 through the A/D converter 20h. The valve element of the directional control valve 12c is moved to the first position by the spring 12d when the first solenoid 12e is deenergized. The valve element of the directional control valve 12c moves to the second position against the biasing force of the spring 12d when the first solenoid 12e is energized.

The nitrogen absorber comprises a bottle in which a nitrogen absorption agent such as zeolite is held. The greater part of the nitrogen of the nitrogen in the air supplied to the nitrogen absorber 12f is absorbed to obtain the oxygen-enriched gas, which contains at least 95% of oxygen gas, by the absorption agent. The mixture of oxygen and remaining nitrogen gas is supplied to the oxygen tank through the conduit 12l.

A solenoid operated shut-off valve 12g is provided in the conduit 12l between the nitrogen absorber 12f and the oxygen tank 12h. The shut-off valve 12g includes a second solenoid 12m which is connected to the output port 20f of the first controller 20 through the solenoid driver 20i. When the second solenoid 12m is deenergized, the shut-off valve 12g separates the nitrogen absorber 12f from the oxygen tank 12h. On the other hand, the nitrogen absorber 12f communicates with the oxygen tank 12h when the second solenoid 12m is energized.

A solenoid operated shut-off valve 12i is provided in the outlet port 12p oxygen tank 12h. The shut-off valve 12i includes a third solenoid 12n which is connected to the output port 20f of the first controller 20 through the solenoid driver 20j. The shut-off valve 12i separates the oxygen tank 12h from the elements provided in the conduit 18 (FIG. 1) downstream of the shut-off valve 12i when the third solenoid 12n is deenergized. On the other hand, the oxygen tank 12h communicates with the downstream elements when the third solenoid 12n is energized. The second and third solenoids 12m and 12n are deenergized to prevent the oxygen-enriched gas from flowing out the tank 12h during the apparatus 10 is stopped.

Figure 5:
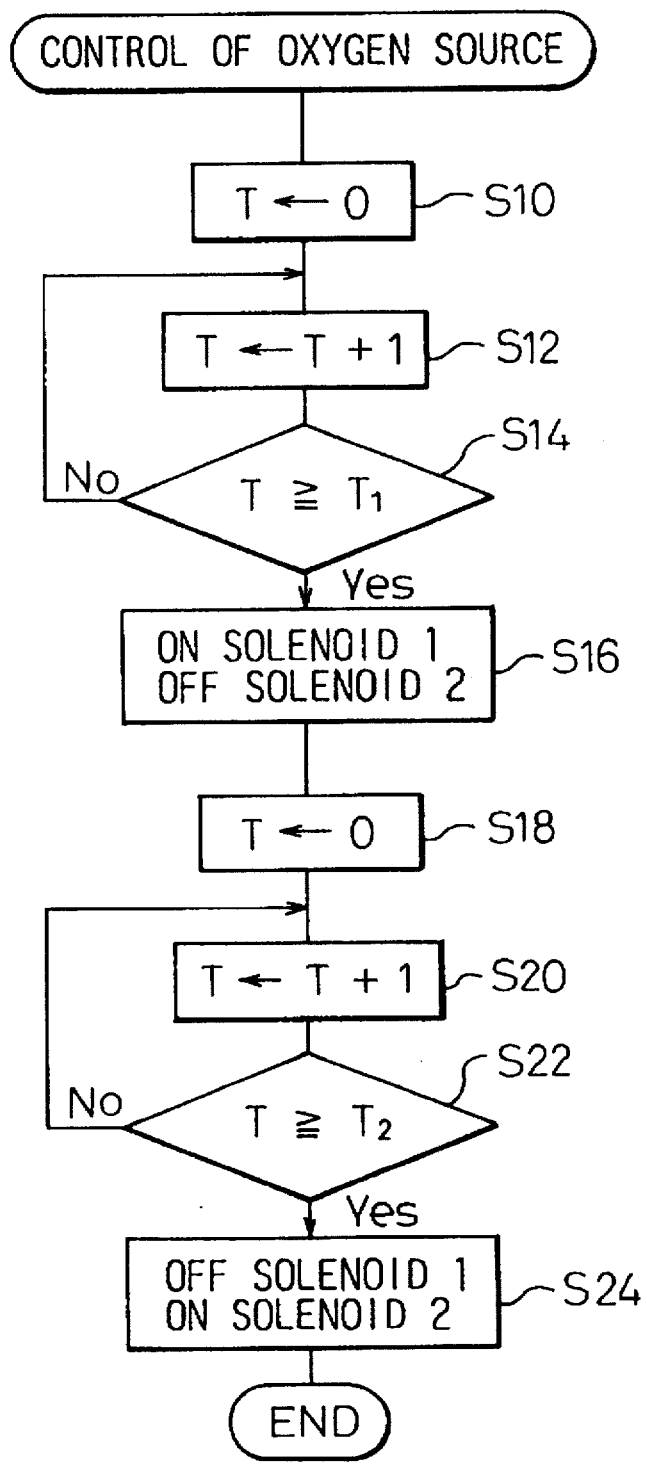
FIG. 5 is a flow chart for controlling the oxygen-enriched gas generating system of FIG. 2.

With reference to FIG. 5, the functional operation of the oxygen source 12 will be described. FIG. 5 illustrates a routine for operating the solenoid operated directional control valve 12c and the solenoid operated shut-off valve 12g.

After starting the compressor 12a, the routine is started. In step S10, zero is input into T. In step S12, one is added to T. In step S14, it is determined that a first predetermined interval $T_1$ has passed or not. Namely, in this step, T is compared with the first interval $T_2$. If T is smaller than $T_2$, the routine returns to step S12. If T is equal to or greater than $T_1$, the routine goes to step S16.

In step S16, the first solenoid 12e of the solenoid operated directional control valve 12c is energized, and the second solenoid 12m of the shut-off valve 12g is deenergized. The element of the directional control valve 12c moves to the second position since the first solenoid 12e is energized. Thus, the discharge port 12j of the compressor 12a is connected to the additional conduit 12b, and the suction port 12k of the compressor 12a is connected to the nitrogen absorber 12f through the conduit 12l. This results in the compressor drawing the gas in the nitrogen absorber 12f and discharging the gas to the ambient through the additional conduit 12b. At the same time, the nitrogen absorber 12f is separated from the oxygen tank 12h. Thus, the pressure in the nitrogen absorber 12f is reduced to remove the absorbed nitrogen from the zeolite.

The process for removing the absorbed nitrogen is continued during a second predetermined interval $T_2$. Namely, in step S18, zero is input into T. In step S20, one is added to T. In step S22, it is determined if the second interval has passed or not. That is, in this step, T is compared with the second interval $T_2$. If T is smaller than $T_2$, the routine returns to step S20. If T is equal to or greater than $T_2$, the routine goes to step S24.

In step S24, the first solenoid 12e of the solenoid operated directional control valve 12c is deenergized, and the second solenoid 12m of the shut-off valve 12g is energized. The valve element of the directional control valve 12c moves to the first position by the spring 12d since the first solenoid 12e is deenergized. Thus, the discharge port 12j of the compressor 12a is connected to the nitrogen absorber 12f, and the suction port 12k of the compressor 12a is connected to the additional conduit 12b. This results in the compressor compressing and supplying the air to the nitrogen absorber 12f. At the same time, the nitrogen absorber 12f communicates with the oxygen tank 12h. Thus, the oxygen-enriched gas is supplied to the oxygen tank 12h.

The above routine is repeated while the apparatus 10 is operated.

The oxygen-enriched gas from the oxygen gas source 12 flows through a conduit or tube 18 which is connected, at an end thereof, to a discharge port 12p (FIG. 2) of the oxygen source 12, and a nasal cannula 36 which is connected to the other end of the conduit 18.

The nasal cannula 36 is of a well known type and is available on the market. The nasal cannula 36 includes a pair of discharge ports 36a and 36b which may be inserted into the the cavitas nasi of the patient to ensure the supply of the respiration gas to the airway of the patient through the cavitas nasi.

The apparatus further comprises a pressure regulating valve 14 which is provided in the conduit 18 for regulating the pressure within the conduit 18 downstream of the valve 14 at a predetermined pressure level, for example 2500 mm $H_2O$-g.

A solenoid operated directional control valve, in this embodiment, a solenoid operated 3-way valve 16 is provided in the conduit 18 down stream of the pressure adjusting valve 14. The solenoid operated 3-way valve 16 has a fourth solenoid 16a, which is connected to the output port 20f through a solenoid driver 20k. The solenoid operated 3-way valve 16 divides the conduit 18 into first and second branch conduits 18a and 18b. Alternatively, a pair of valves can be used to divide the conduit 18 into the first and second branch conduits 18a and 18b.

on the first branch conduit 18a, a first adjustable flow reducer 24 for adjusting the flow rate through the first branch conduit 18a, and a humidifier 28 for adding the humidity in the oxygen-enriched gas for the patient are provided. The first adjustable flow reducer 24 can be of any type known in the art. However, in the preferred embodiment, the adjustable flow reducer 24 is of a type which is described in Japanese Unexamined Patent Publication (Kokai) No. 62-140026. The flow reducer of JPP '026 comprises a housing which has inlet and outlet ports, and a ring held in the housing. The ring includes apertures of various radius, and is rotatable in the housing to align one of the apertures with a discharge port on the housing. A gas axially flows into the housing and radially flows out through one aperture which is aligned to the discharge port, and the flow rate is reduced to a desired rate by the aperture.

On the second branch conduit 18b, a second adjustable flow reducer 26 is provided. The second adjustable flow reducer 26 can be of any type known in the art, and in particular, the second adjustable flow reducer 26 can be an variable orifice available on the market. The first and second branch conduits 18a and 18b combine downstream of the humidifier 28 into the conduit 18. Another humidifier (not shown) can be provided in the second branch conduit 18b. Further, the humidifier 28 can be provided in the conduit 18 downstream of the confluence.

A flow sensor 30 is provided in the conduit 18 downstream of the confluence of the first and second branch conduit 18a and 18b, and is connected to the input port 20e of the first controller 20 through an A/D converter 20g. The flow sensor 30 can be of any type known in the art such as an area flow meter, a hot wire flow meter, an electromagnetic flow meter, an ultrasonic flow meter, mass flow meter, and a vortex flow meter. Alternatively, the pressure difference, between the upstream of the 3-way valve 16 and the downstream of the confluence, can be detected to obtain the flow rate.

A solenoid operated shut-off valve 32 is provided in the conduit 18 downstream of the flow sensor 30, in particular, adjacent to the nasal cannula 36. The solenoid operated shut-off valve 32 has a fifth solenoid 32a which is controlled by a second controller 22.

The second controller 22 comprises a random access memory (RAM) 22a, a read-only memory (ROM) 22b, central processing unit (CPU) 22c, an output port 22f and an input port 22e which are connected to each other by a bidirectional bus 22d. The fifth solenoid 32a is connected to the output port 22f through a solenoid driver 22i. When the fifth solenoid 32a is energized, the shut-off valve 32 fluidly connects the nasal cannula 36 to the oxygen source 12. On the other hand, when the fifth solenoid 32a is deenergized, the shut-off valve 32 fluidly separates the nasal cannula 36 from the oxygen source 12.

A pressure sensor 34 is provided in the conduit 18 downstream of the shut-off valve 32 to detect the changes in the pressure of the respiratory gas for the patient. The pressure sensor 34 is connected to the input port 22e of the second controller 22 through an A/D converter 22h.

The apparatus 10 is further provided with a selector 40 for switching the mode of the operation of the apparatus 10 between intermittent and continuous modes. The selector 40 comprises, in this embodiment, a contact 40a which is connected to the input port 22e through an A/D converter 22i, and a direct voltage source 40b. The voltage from the selector 40 is converted into a digital signal by the A/D converter and stored in the RAM 22a as a flag for switching the operation of the apparatus 10 between intermittent and continuous modes.

The apparatus 10 is further provided with an interval input device 38 which is connected to the input port 22e of the second controller 22 through an A/D converter 22g. The interval input device 38 can be formed, for example, by a variable resistor (not shown) which is connected to a direct voltage source (not shown). The voltage is converted into a digital signal by the A/D converter 22g and stored in the RAM 22a as an interval when the solenoid 32a of the shut-off valve 32 is energized.

Figure 6:
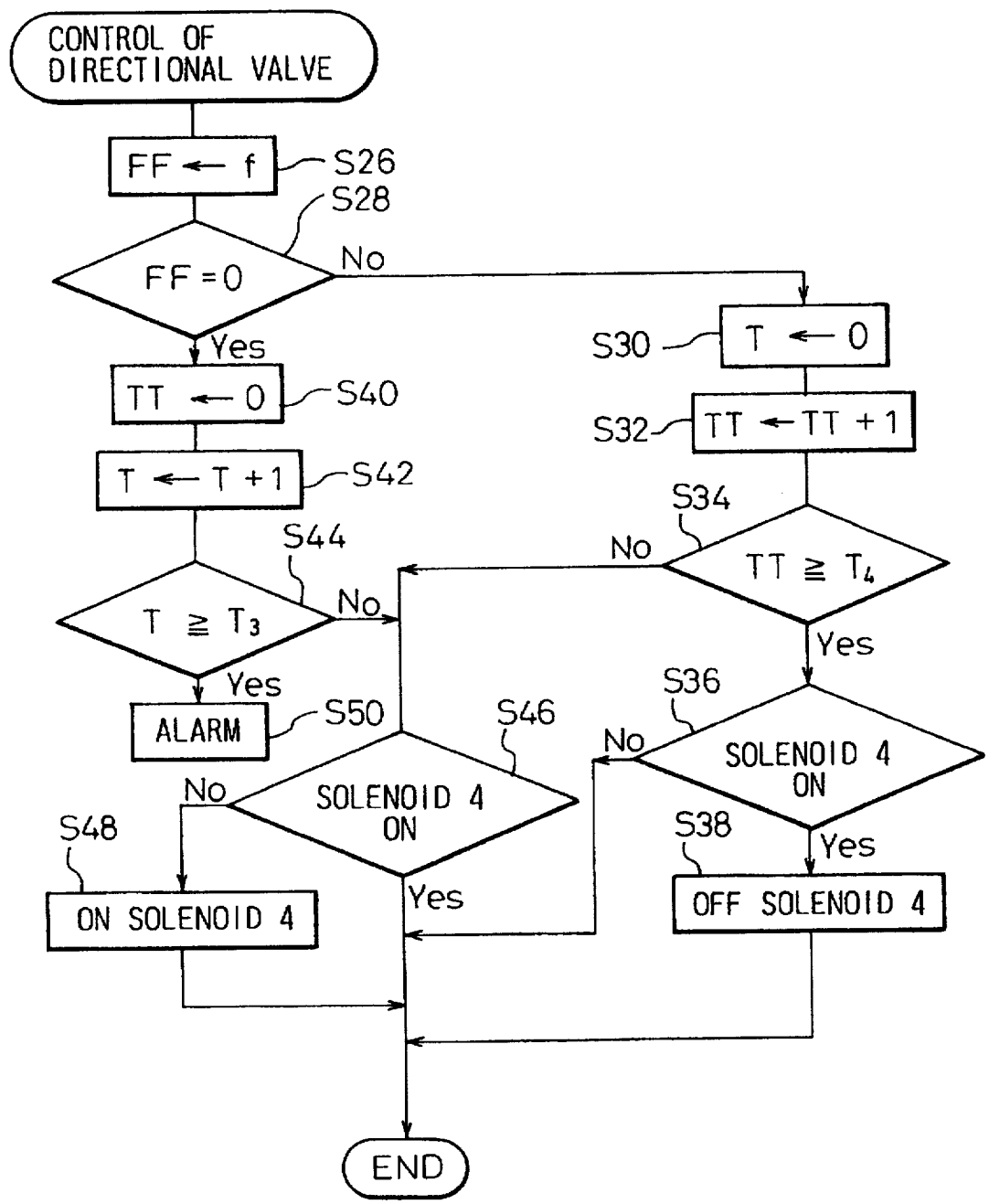
FIG. 6 is a flow chart for controlling a shut-off valve to provide intermittent and continuous modes to the apparatus according to the invention.
Figure 7A:
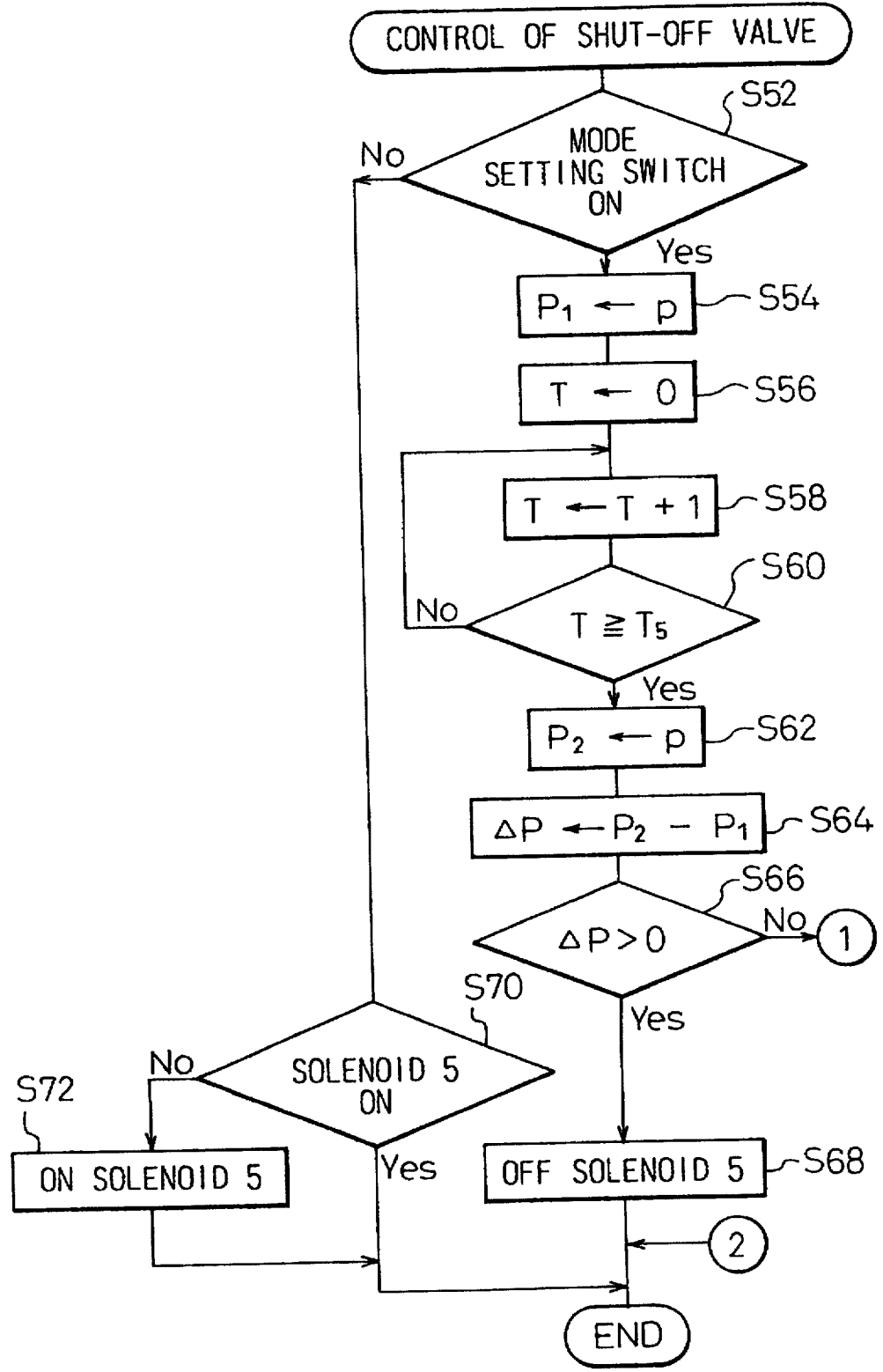
FIG. 7A is a flow chart for controlling a directional valve of the apparatus according to the invention.
Figure 7B:
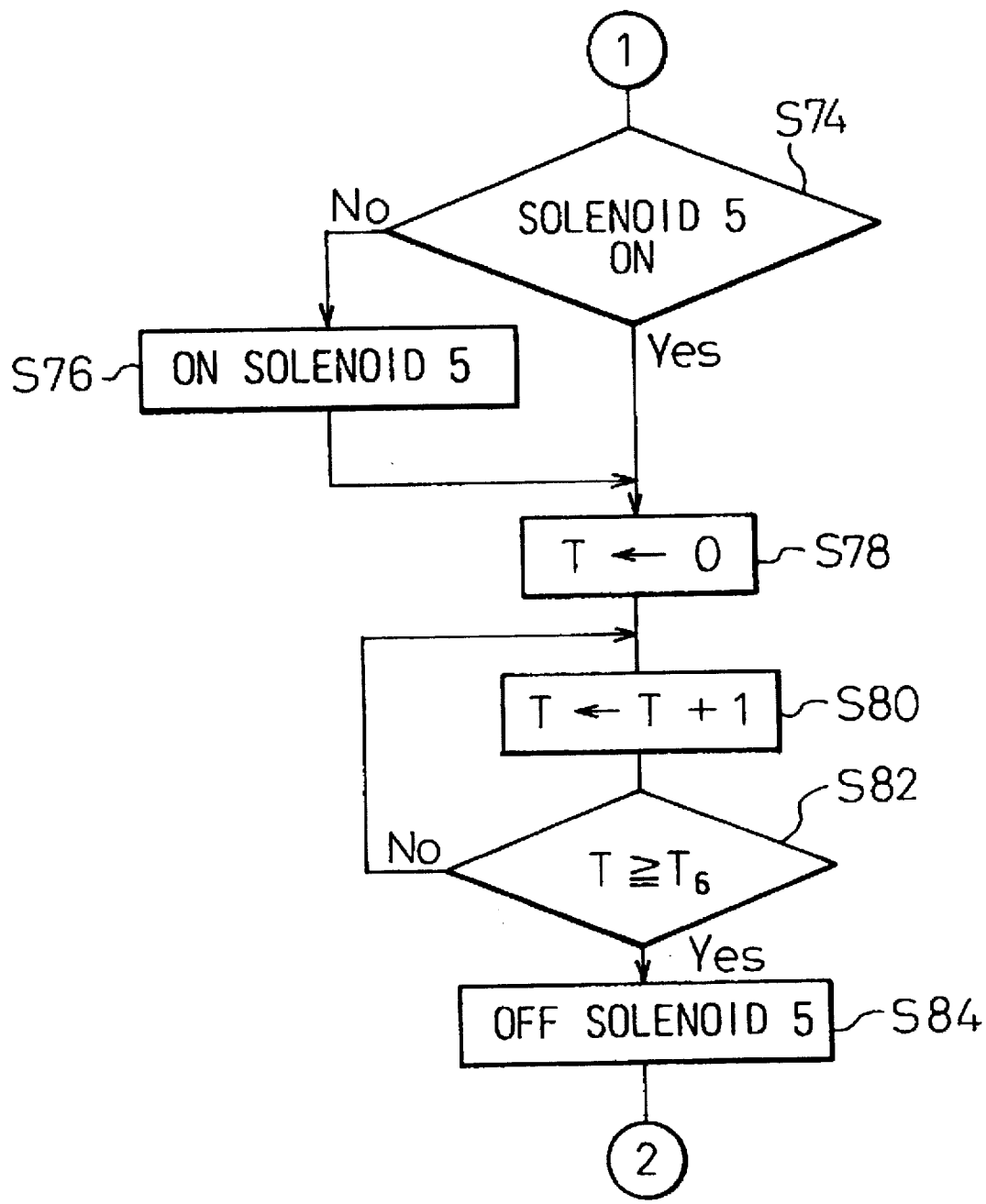
FIG. 7B is a flow chart for controlling a directional valve of the apparatus according to the invention.

With reference to FIGS. 6, 7A and 7B, the functional operation of the apparatus 10 will be described.

FIG. 6 illustrates a routine for controlling the directional control valve or 3-way valve 16, and FIGS. 7A and 7B illustrate a routine for controlling the shut-off valve 32.

In FIGS. 7A and 7B, in step S52, it is determined whether the selector or mode setting switch 40 is on or off. If the selector 40 is off, it is determined that the continuous mode is selected, and the routine goes to step S70. In step S70, it is determined whether the fifth solenoid 32a of the shut-off valve 32 is energized or deenergized. If the fifth solenoid 32a is energized the routine is ended and repeated from the step S52 again. If the fifth solenoid 32a is deenergized, the routine goes to step S72, in which the fifth solenoid 32a is energized to fluidly connects the nasal cannula 36 to the oxygen source 12. After this, the routine is ended and repeated from the step S52 again.

In step S52, if the selector 40 is on, it is determined that the intermittent mode is selected, and the routine goes to step S54. In step S54, the pressure within the conduit 18 is detected by the pressure sensor 34, and the detected pressure value is input into $P_1$ through the A/D converter 22h.

In step S56, zero is input into T. In step S58, one is added to T. In step S60, it is determined if a fifth predetermined interval $T_5$ has passed or not. The fifth interval is a time used to differentiate the pressure, and can be preferably selected to be 10 msec as an example. Thus, in step S60, T is compared with the fifth interval $T_5$. If T is smaller than $T_5$, the routine returns to step S58. If T is equal to or greater than $T_5$, the routine goes to step S62.

After the fifth interval has passed, the routine goes to step S62. In step S62, the pressure within the conduit 18 is detected again by the pressure sensor 34, and the detected pressure value is input into In step S64, the difference between $P_2$ and $P_1$ is input into a $\Delta$ P as a time differential value of the pressure. In step S66, the time differential value of the pressure $\Delta P$ is determined, whether a $\Delta P$ is positive or not, to obtaine the respiration phase. If $\Delta P$ is positive, the expiration phase is detected, and the routine goes to step S68. On the other hand, if $\Delta P$ is zero or negative, the inspiration phase is detected, and the routine goes to step S74 (FIG. 7B). During the expiration phase, the shut-off valve 32 separates the nasal cannula 36 from the oxygen source 12 to prevent the supply of the respiratory gas. Thus, in step S68, the fifth solenoid 32a of the shut-off valve 32 is deenergized.

When the inspiration phase is detected in step S66, the shut-off valve 32 fluidly connects the nasal cannula 36 to the oxygen source 12 to supply the respiratory gas to the patient. In step S74, it is determined whether the fifth solenoid 32a of the shut-off valve 32 is energized or deenergized. If the fifth solenoid 32a is energized the routine goes to step S78. If the fifth solenoid 32a is deenergized, the routine goes to step S76. In step S76, the fifth solenoid 32a is energized to fluidly connects the nasal cannula 36 to the oxygen source 12.

In step S78, zero is input into T. In step S80, one is added to T. In step S82, it is determined if a sixth interval $T_6$, has passed or not. Namely, in this step, T is compared with the sixth interval $T_6$. If T is smaller than $T_6$, the routine returns to step S58. If T is equal to or greater than $T_6$, the routine goes to step S84. After the predetermined time has passed, the routine goes to step S84 in which the fifth solenoid 32a is deenergized to separate the nasal cannula 36 from the oxygen source 12, and the above routine is repeated from the step S52 again.

As described in the above according to one feature of the invention, the respiratory gas is supplied to the patient only during a predetermined time at the starting stage of the inspiration phase, preferably a time which corresponds to one third of the mean time for the respiration, to save the respiratory gas which cannot reach the lungs of the patient and is exhausted by the expiratory gas from the lungs during the sequence expiration phase. The predetermined time can be determined within a range from about 30 msec to 2 sec. In the intermittent mode, the respiratory gas is supplied to a patient at a relatively large flow rate in the form of a pressure pulse to compensate for a flow rate prescribed by a doctor since the respiratory gas is supplied only during a short time at the starting stage of the inspiration phase. The flow rate can be determined within a range from 0.3 CC/sec to 130 CC/sec.

FIG. 6 illustrates a routine for controlling the directional control valve or 3-way valve 16. The 3-way valve 16 is controlled so that the respiratory gas is supplied to the patient through the first branch conduit 18a when the continuous mode is selected, and through the second branch conduit 18b when the intermittent mode is selected.

In step S26, the flow rate of the respiratory gas within the conduit 18 is detected by the flow sensor 30, and the detected flow rate value is input into FF.

In step S28, it is determine whether FF=0 or not. If FF=0, it is not determined that the continuous mode is selected, and the routine goes to step S40. If not, it is determined that one of the intermittent and continuous modes is selected, and the routine goes to step S30.

In step S40, zero is input into TT. In step S42, one is added to T. In step S44, it is determined whether a third predetermined time has passed or not. The third predetermined time will be described hereinafter. That is, in step S44, it is determined whether T is equal to or greater than a third interval $T_3$ or not. If T is smaller than $T_3$, the routine goes to step S46.

In step S46, it is determined whether the fourth solenoid 16a of the 3-way valve 16 is energized or not. If the fourth solenoid 16a is deenergized, the routine goes to step S48 in which the fourth solenoid 16a is energized to supply the respiratory gas to the patient through the second branch conduit 18b. Through the second branch conduit, the flow rate of the respiratory gas is reduced, to a suitable rate for the intermittent mode, by the second adjustable flow reducer 26. The adjustable flow reducer 26 is adjusted so that a maximum flow rate, which is required during the intermittent mode, can flow through the second branch conduit 18b.

As mentioned above, if FF=0 in step S28, it is apparent that the continuous mode is not selected. However, if not, it is not apparent whether the continuous mode or the intermittent mode is selected. According to the invention, it is determined that the continuous mode is selected if the condition of FF≠0 continues for at least a fourth predetermined time.

In step S30, zero is input into T. In step S32, one is added to TT. In step S34, it is determined whether the fourth predetermined time has passed or not. That is, in step S34, it is determined whether TT is equal to or greater than a fourth interval $T_4$ or not. If TT is smaller than $T_4$, the routine goes to step S46. If not, the routine goes to step S36.

In step S36, it is determined whether the fourth solenoid 16a of the 3-way valve 16 is energized or not. If the fourth solenoid 16a is energized, the routine goes to step S38 in which the fourth solenoid 16a is deenergized to supply the respiratory gas to the patient through the first branch conduit 18a. Through the first branch conduit 18a, the flow rate of the respiratory gas is reduced to a suitable rate for the continuous mode by the first adjustable flow reducer 24. The adjustable flow reducer 24 is adjusted so that a flow rate prescribed by a doctor is supplied to the patient. If the fourth solenoid 16a is deenergized in step S36, the routine is ended and repeated from step S26 again.

In step S30, as mentioned above, zero is input into T. Thus, after the first time when FF=0 is determined in step S28, T starts to increase. When the condition of FF=0 continues for at least the third predetermined time, it means that a malfunction has occurred in the apparatus. Thus, if T is equal to or greater than the predetermined interval $T_3$ in step S44, the routine goes to step S50 in which an alarm (not shown) is activated to prevent an accident.

As described above, in the intermittent mode, the respiratory gas is supplied to a patient at a relatively large flow rate in the form of a pressure pulse to compensate for a flow rate prescribed by a doctor since the respiratory gas is supplied only during a short time at the starting stage of the inspiration phase. However, if a long tube, which corresponds to the conduit 18, is used to extend the action range of the patient, a delay occurs until the pressure pulse reaches the discharge port of the nasal cannula. According to the invention, the shut-off valve 32 is provided adjacent to the nasal cannula 36 to prevent the delay. Preferably, the shut-off valve 32 is provided adjacent to the nasal cannula so that the delay is reduced to a level smaller than 40 msec. If the delay is greater than the level of 40 msec, the apparatus cannot supply the respiration gas to the patient appropriately. In the most preferable embodiment, the delay is reduced to a level-smaller than 40 msec, preferably to a level smaller than 20 msec. Further, when the conduit 18 has length 5 to 20 m or more, the shut-off valve 32 is provided in the conduit 18 at a position 2 to 5 m, and most preferably at a position shorter than 2 m, from the ends of the discharge ports 36a and 36b.

Figure 3:
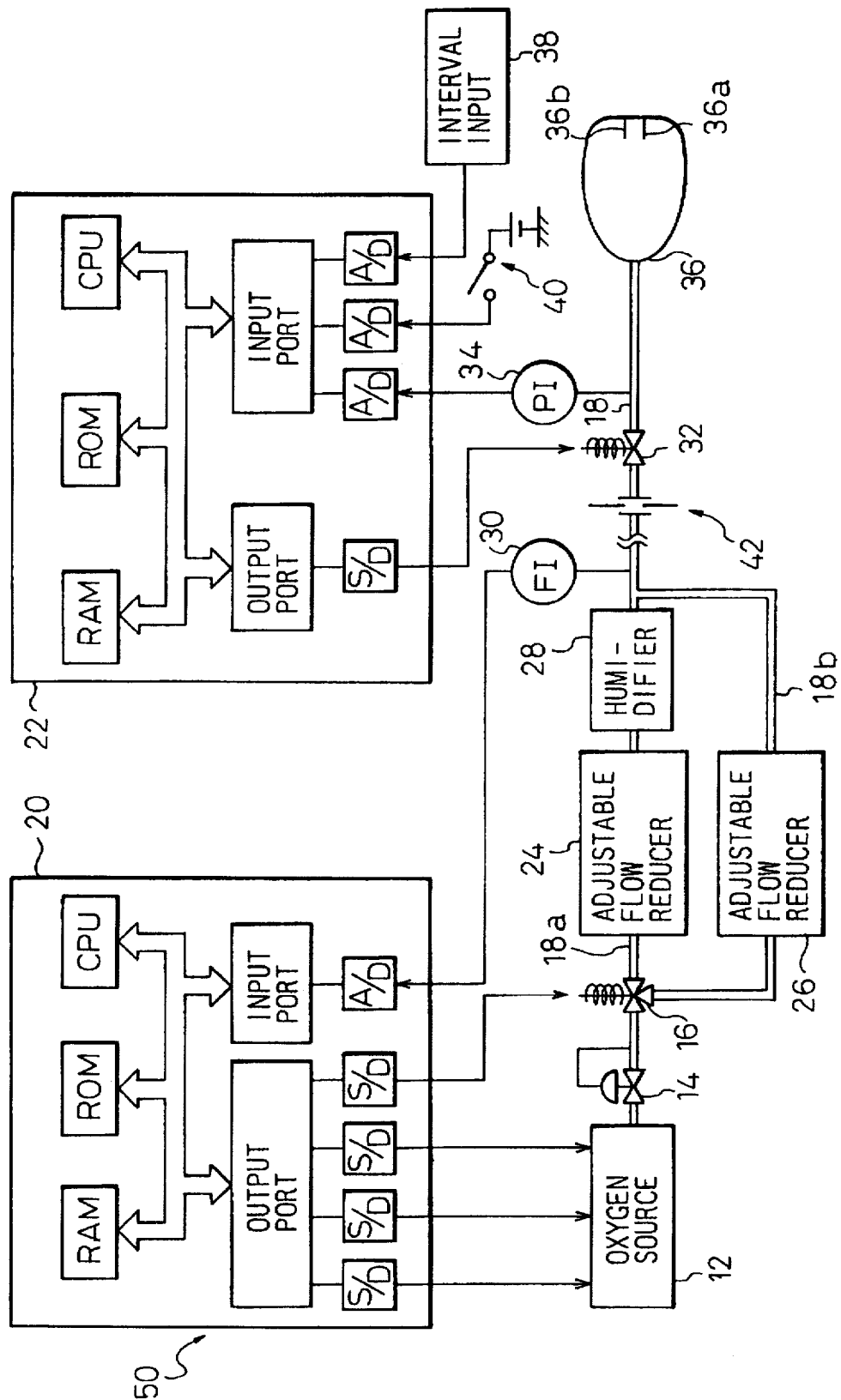
FIG. 3 is schematic diagram of an apparatus according to the second embodiment of the invention.

With reference to FIG. 3, the second embodiment of the invention will be described.

In FIG. 3, an apparatus 50, according to the second embodiment, is substantially the same as in the first embodiment, except that, in the second embodiment, the apparatus 50 is provided with an orifice 42 on the conduit 18 upstream of the shut-off valve 32. Therefore, the elements similar to those in the first embodiment are indicated by the same reference numbers.

In the first embodiment, the shut-off valve 32 is provided in the conduit 18 adjacent to the nasal cannula 36. However, if a portion of the conduit 18 upstream of the shut-off valve 32 is relatively long, the pressure pulse of the respiratory gas supplied to the patient becomes too large due to the effect of the upstream conduit portion. The orifice 42 blocks the effect of the upstream conduit portion, and prevents the pressure pulse from becoming too large.

Figure 4:
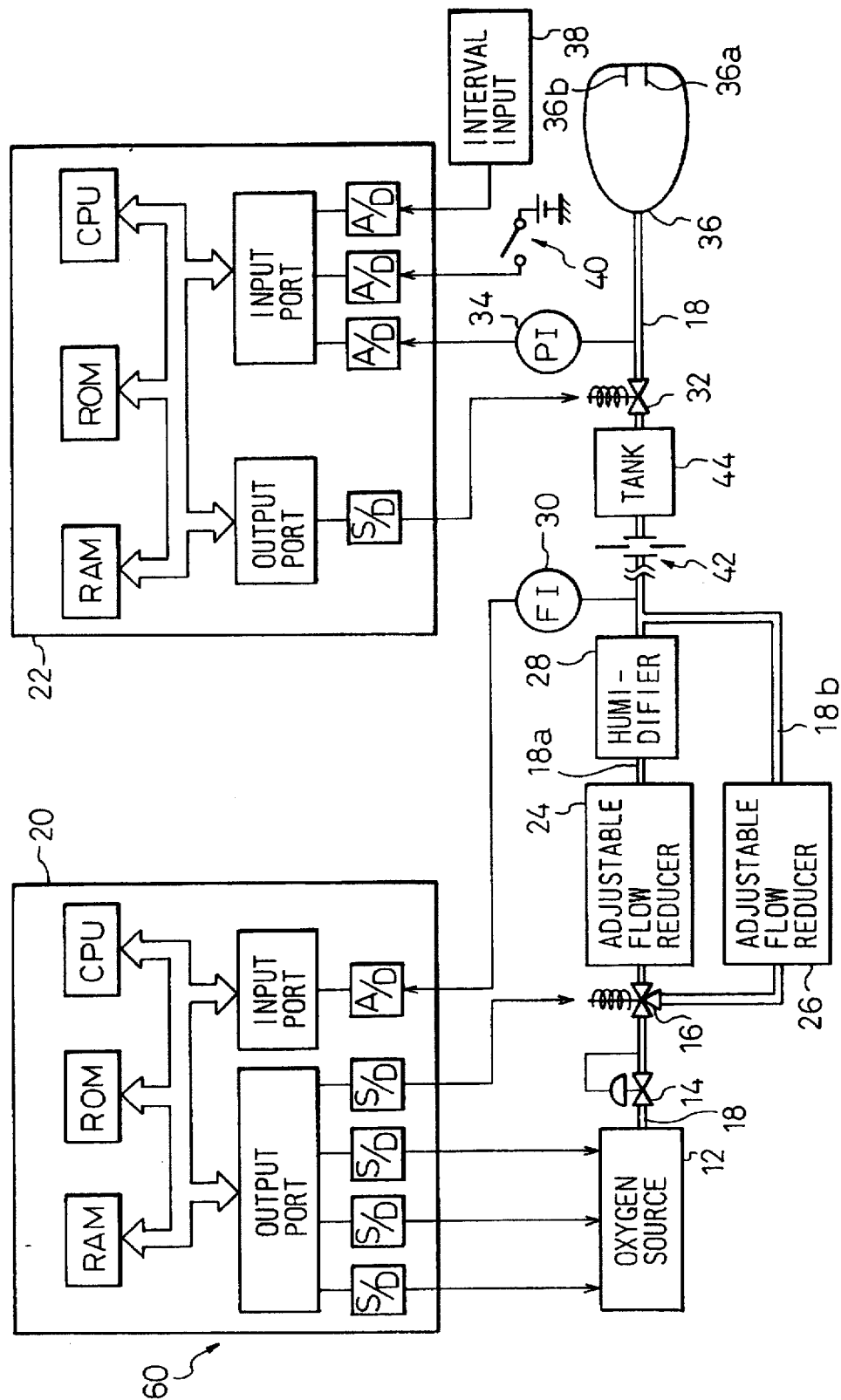
FIG. 4 is schematic diagram of an apparatus according to the third embodiment of the invention.

With reference to FIG. 4, the third embodiment of the invention will be described.

In FIG. 4, an apparatus 60, according to the third embodiment, is substantially the same as in the second embodiment, except that, in the third embodiment, the apparatus 60 is further provided with a tank 44 on the conduit 18 upstream of the orifice 42. Therefore, the elements similar to those in the first and second embodiments are indicated by the same reference numbers.

In the second embodiment, the orifice 42 is provided in the conduit 18 upstream of the shut-off valve 32. However, if a portion of the conduit 18 between the orifice 42 and the shut-off valve 32 is relatively small, insufficient pressure pulse of the respiratory gas is supplied to the patient since the orifice 42 blocks the effect of the upstream conduit portion. The tank 44 functions an accumulator to provide a sufficient pressure pulse. The volume of the tank 44 can be selected to a level, preferably 100 ml, which is sufficient to provide an appropriate pressure pulse. If the portion of the conduit 18 between the orifice 42 and the shut-off valve 32 has sufficient volume, the conduit portion functions as an accumulator and the tank 44 can be removed.

Figure 8:
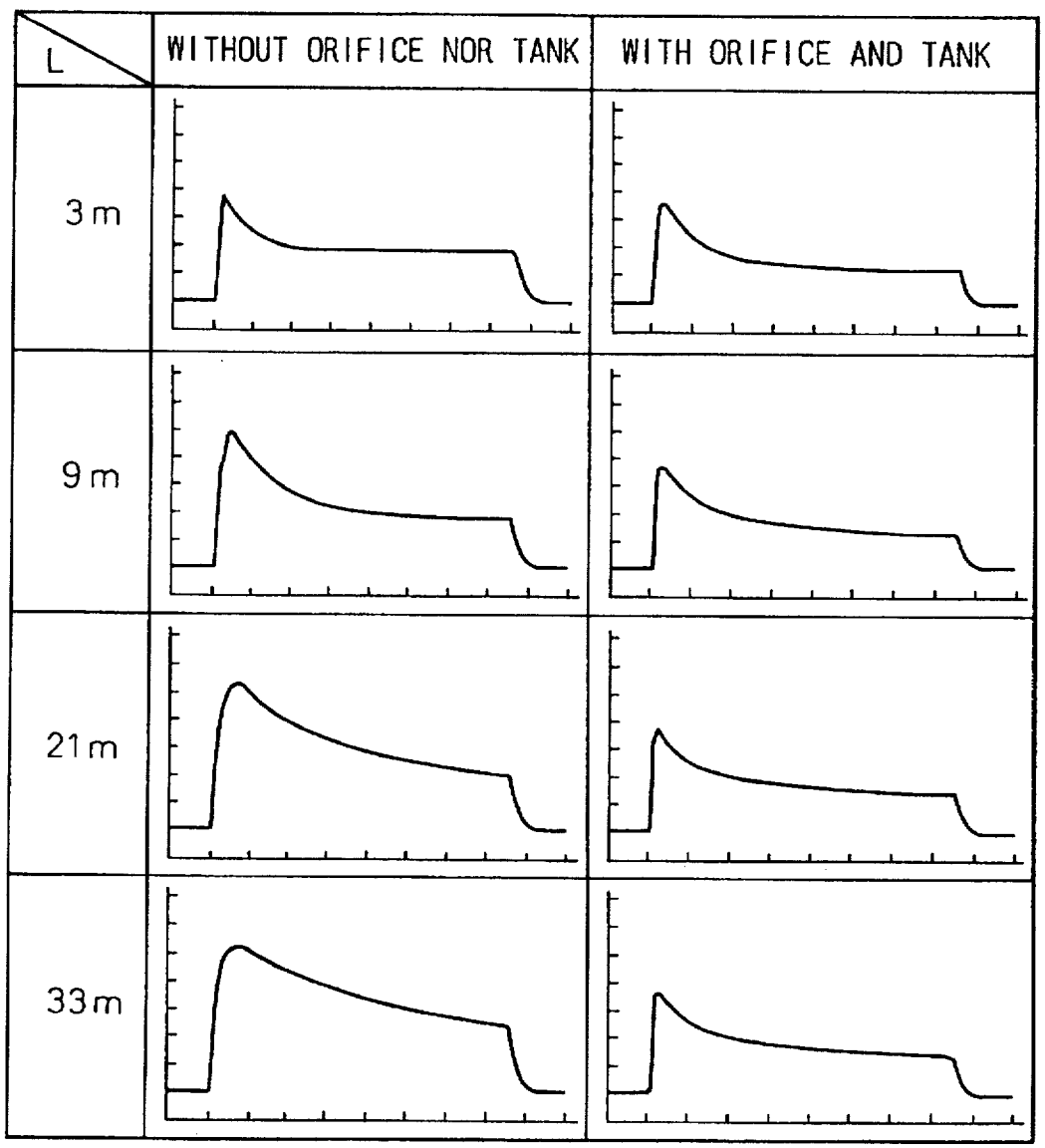
FIG. 8 shows experimental data and illustrates the effect of an orifice and a tank provided in a conduit upstream of the shut-off valve.

In FIG. 8, the effects of the orifice 42 and the tank 44, which were experimentally obtained, are illustrated. In the respective graphs, the horizontal lines represent time, and the vertical lines represent pressure. If neither the orifice 42 nor the tank 44 are provided, the longer conduit 18 produces a larger pressure pulse. On the other hand, if the orifice 42 and the tank 44 are provided, the pressure pulse is substantially constant when the length of the conduit 18 is changed.

Figure 9:
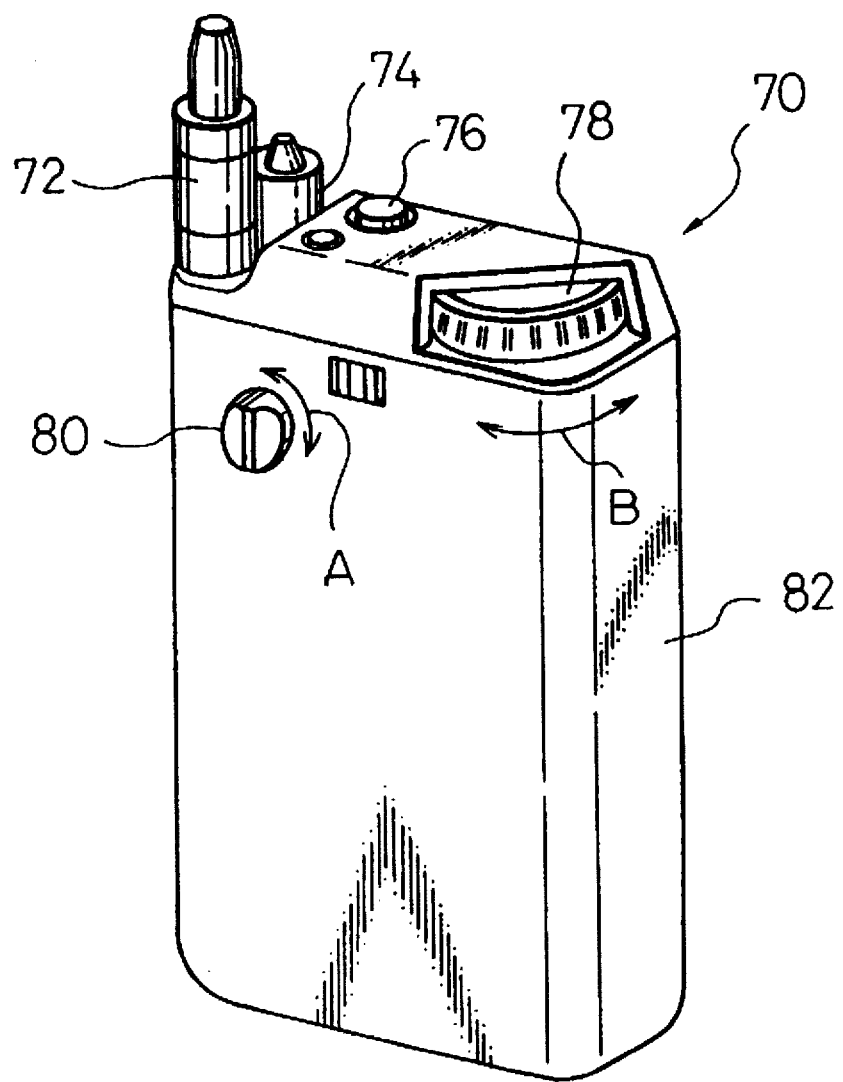
FIG. 9 is a perspective view of a manual control unit of the invention.

With reference to FIG. 9, a manual control unit of the invention will be described.

The manual control unit is adapted to be put near a patient or on a patient who uses the apparatus, and to be used for controlling the operation of the shut-off valve between the intermittent and continuous modes, and for adjusting the interval during which the shut-off valve fluidly connects the nasal cannula to the oxygen source in the intermittent mode. The manual control unit comprises a housing 70 in which the second controller 22, the pressure sensor 32, the shut-off valve 32, the selector 40, the interval input device 38, the orifice 42, and the tank 44 are provided. The manual control unit comprises an inlet connector 74 to which the conduit 18 is connected, and an outlet connector to which the nasal cannula is connected. The inlet and outlet connectors are connected to each other through a conduit or tube (not shown) which forms a part of the conduit 18, and is enclosed by the housing 70. The manual control unit further comprises an on-off switch 76, a knob 80, which is-rotational in an allow A, for operating the selector 40 between on and off position, and a dial 78, which is rotational in an allow B, for continuously operating the interval input device 38. The knob 80 can include a stem (not shown) which extends along the rotational axis of the knob 80 and connected to the shut-off valve 32 to open the valve element of the shut-off valve 32 when the continuous mode is selected.

It is further understood by those skilled in the art that the forgoing description is a preferred embodiment of the disclosed device and that various changes and modifications may be made without departing from the spirit and scope of the invention.

We claim:

1. An apparatus for supplying a respiratory gas to a patient comprising:

means for generating a respiratory gas;

means for introducing the respiratory gas into a patient's cavitas nasi, the introducing means including an output port which is adapted to be inserted into a patient's cavitas nasi;

a conduit fluidly connected to the respiratory gas generating means and the introducing means;

a valve means, provided in the conduit, for separating and connecting the introducing means from and to the respiratory gas generating means; and an orifice provided in the conduit upstream of the valve means for limiting the pressure of the respiratory gas introduced to a patient;

means for controlling the operation of the valve means between an intermittent and continuous mode such that, in the intermittent mode, the valve means connects the introducing means to the respiratory gas generating means at a predetermined interval to provide the respiratory gas in the form of a pulse or, in the continuous mode, the valve means continuously connects the introducing means to the respiratory gas generating means; and the valve means being provided in the conduit adjacent to the introducing means to allow the pressure pulse of the respiratory gas to reach the output port of the introducing means without a delay greater than 40 msec during the intermittent mode.

2. An apparatus according to claim 1, further comprising an orifice provided in the conduit upstream of the valve means so as to limit excess respiratory gas flow when the valve means opens.

3. An apparatus according to claim 2 further comprising an accumulator means provided in the conduit between the orifice and the valve means.

4. An apparatus according to claim 1 further comprising means for detecting an inspiration phase; and the valve means connecting the introducing means to the respiratory gas generating means during a predetermined time after the inspiration phase is detected.

5. An apparatus according to claim 4 in which the valve means connects the introducing means to the respiratory gas generating means during a predetermined time, which is shorter than one third of the interval of the respiration phase, after the inspiration phase is detected.

6. An apparatus according to claim 1 further comprising first and second branches which are divided from the conduit;

first and second flow reducers provided in the first and second branch conduits respectively; and a directional valve means for selecting one of the first and second branch conduits through which the respiration gas flows to the patient.

7. An apparatus according to claim 6 in which the apparatus further comprises means for determining whether the continuous mode or intermittent mode is selected; and the directional valve means allowing the respiratory gas to flow through the first branch conduit during the continuous mode, and to flow through the second branch conduit during the intermittent mode; and the first flow reducer reduces the flow rate of the respiratory gas more than the second flow reducer.

8. An apparatus according to claim 1 further comprising a manual control unit which comprises:

a housing in which the valve means is provided;

an inlet connector to which the conduit is connected;

an outlet connector to which the introducing means is connected;

a selector switch for manually selecting the operational mode between the intermittent and continuous modes; and an interval input device for selecting the interval during which the valve means fluidly connects the introducing means to the respiratory gas generating means.

9. An apparatus for supplying a respiratory gas to a patient comprising:

means for generating a respiratory gas;

means for introducing the respiratory gas into a patient's cavitas nasi, the introducing means including an output port which is adapted to be inserted into a patient's cavitas nasi;

a conduit fluidly connected to the respiratory gas generating means and the introducing means;

a valve means, provided in the conduit, for separating and connecting the introducing means from and to the respiratory gas generating means;

an orifice provided in the conduit upstream of the valve means for limiting the pressure of the respiratory gas introduced to a patient;

means for controlling the operation of the valve means between intermittent and continuous mode such that, in the intermittent mode, the valve means connects the introducing means to the respiratory gas generating means at a predetermined interval to provide the respiratory gas in the form of a pulse, in the continuous mode, the valve means continuously connects the introducing means to the respiratory gas generating means; and the valve means being provided in the conduit within 2 m from an end of the output port.

10. An apparatus according to claim 9, further comprising an orifice provided in the conduit upstream of the valve means so as to limit excess respiratory gas flow when the valve means opens.

11. An apparatus according to claim 10 further comprising an accumulator means provided in the conduit between the orifice and the valve means.

12. An apparatus according to claim 11 further comprising a first and second branches which are divided from the conduit;

first and second flow reducers provided in the first and second branch conduits respectively; and a directional valve means for selecting one of the first and second branch conduits through which the respiration gas flows to the patient.

13. An apparatus according to claim 12 in which the apparatus further comprises means for determining whether the continuous mode or intermittent mode is selected;

the directional valve means allowing the respiratory gas to flow through the first branch conduit during the continuous mode, and to flow through the second branch conduit during the intermittent mode; and the first flow reducer reduces the flow rate of the respiratory gas more than the second flow reducer.

14. An apparatus according to claim 10 further comprising a manual control unit which comprises:

housing in which the valve means is provided;

an inlet connector to which the conduit is connected;

an outlet connector to which the introducing means is connected;

a selector switch for manually selecting the operational mode between the intermittent and continuous modes; and an interval input device for selecting the interval during which the valve means fluidly connects the introducing means to the respiratory gas generating means.

15. An apparatus according to claim 11 further comprising means for determining whether the continuous mode or intermittent mode is selected; and the valve means connecting the introducing means to the respiratory gas generating means during a predetermined time after the inspiration phase is detected.

16. An apparatus according to claim 15 in which the valve means connects the introducing means to the respiratory gas generating means during a predetermined time, which is shorter than one third of the interval of the respiration phase, after the inspiration phase is detected.

17. An apparatus for supplying a respiratory gas to a patient comprising:

means for generating a respiratory gas;

means for introducing the respiratory gas into a patient's cavitas nasi, the introducing means including an output port which is adapted to be inserted into a patient's cavitas nasi;

a conduit fluidly connected to the respiratory gas generating means and the introducing means;

a valve means, provided in the conduit, for separating and connecting the introducing means from and to the respiratory gas generating means;

an orifice provided in the conduit upstream of the valve means for limiting the pressure of the respiratory gas introduced to a patient;

means for controlling the operation of the valve means between an intermittent and continuous mode such that, in the intermittent mode, the valve means connects the introducing means to the respiratory gas generating means at a predetermined interval to provide the respiratory gas in the form of a pulse or, in the continuous mode, the valve means continuously connects the introducing means to the respiratory gas generating means; and an accumulator means providing in the conduit between the orifice and the valve means.

18. An apparatus for Supplying a respiratory gas to a patient comprising:

means for generating a respiratory gas;

means for introducing the respiratory gas into a patient's cavitas nasi, the introducing means including an output port which is adapted to be inserted into a patient's cavitas nasi;

a conduit fluidly connected to the respiratory gas generating means and the introducing means;

a valve means, provided in the conduit, for separating and connecting the introducing means from and to the respiratory gas generating means;

an orifice provided in the conduit upstream of the valve means;

means for controlling the operation of the valve means between an intermittent and continuous mode such that, in the intermittent mode, the valve means connects the introducing means to the respiratory gas generating means at a predetermined interval to provide the respiratory gas in the form of a pulse or, in the continuous mode, the valve means continuously connects the introducing means to the respiratory gas generating means;

first and second branches which are divided from the conduit;

first and second flow reducers provided in the first and second branch conduits, respectively; and a directional valve means for selecting one of the first and second branch conduits through which the respiration gas flows to the patient.

19. An apparatus for supplying a respiratory gas to a patient comprising:

means for generating a respiratory gas;

means for introducing the respiratory gas into a patient's cavitas nasi, the introducing means including an output port which is adapted to be inserted into a patient's cavitas nasi;

a conduit fluidly connected to the respiratory gas generating means and the introducing means;

a valve means, provided in the conduit, for separating and connecting the introducing means from and to the respiratory gas generating means;

an orifice provided in the conduit upstream of the valve means;

means for controlling the operation of the valve means between an intermittent and continuous mode such that, in the intermittent mode, the valve means connects the introducing means to the respiratory gas generating means at a predetermined interval to provide the respiratory gas in the form of a pulse or, in the continuous mode, the valve means continuously connects the introducing means to the respiratory gas generating means; and a manual control unit comprising:

a housing in which the valve means is provided;

an inlet connector to which the conduit is connected;

an outlet connector to which the introducing means is connected;

a selector switch for manually selecting the operational mode between the intermittent and continuous modes; and an interval input device for selecting the interval during which the valve means fluidly connects the introducing means to the respiratory gas generating means.

* * * * *